United States Patent [19]

Wagner et al.

[11] Patent Number: 4,905,521
[45] Date of Patent: Mar. 6, 1990

[54] PORTED JACKET FOR USE IN DEFORMATION MEASUREMENT APPARATUS

[75] Inventors: Leslie A. Wagner; Paul E. Senseny; Kirby D. Mellegard; Steven B. Olsberg, all of Rapid City, S. Dak.

[73] Assignee: RE/SPEC Inc., Rapid City, S. Dak.

[21] Appl. No.: 285,548

[22] Filed: Dec. 16, 1988

[51] Int. Cl.⁴ .............................................. G01N 3/00
[52] U.S. Cl. ........................................ 73/794; 73/818
[58] Field of Search ................ 73/794, 795, 796, 797, 73/798, 825, 818, 819, 820, 821, 822, 824

[56] References Cited

U.S. PATENT DOCUMENTS

| | | | |
|---|---|---|---|
| 3,199,341 | 8/1965 | Heuer, Jr. | 73/94 |
| 3,505,860 | 4/1970 | Bishop | 73/94 |
| 3,616,685 | 11/1971 | Strom | 73/84 |
| 4,047,425 | 9/1977 | Handy | 73/94 |
| 4,122,704 | 10/1978 | Lutenegger | 73/822 |
| 4,562,726 | 1/1986 | Barnaby | 73/38 |
| 4,579,003 | 4/1986 | Riley | 73/794 X |
| 4,599,891 | 7/1986 | Brauer | 73/38 |

Primary Examiner—Jerry W. Myracle
Attorney, Agent, or Firm—Kinney & Lange

[57] ABSTRACT

A device for allowing deformation measurement of a jacketed specimen when the specimen is loaded includes an elastomeric specimen container or jacket surrounding a specimen while the specimen is being loaded by a test apparatus. The specimen jacket wall is compressible, and the wall follows and allows deformation of the specimen. The jacket wall of compressible material is provided with at least one opening and a thin layer or shim of substantially non-compressible (metal) material covers and seals this opening. An extensometer is then positioned with its specimen engaging contact members engaging the substantially non-compressible material to measure the deformation of the specimen when the specimen is loaded, without compressibility effects of the jacket.

16 Claims, 4 Drawing Sheets

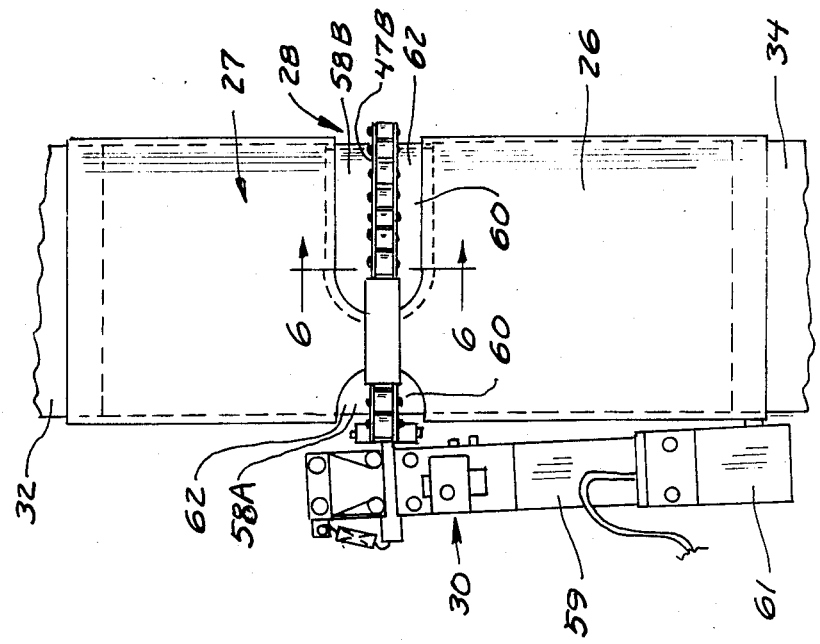
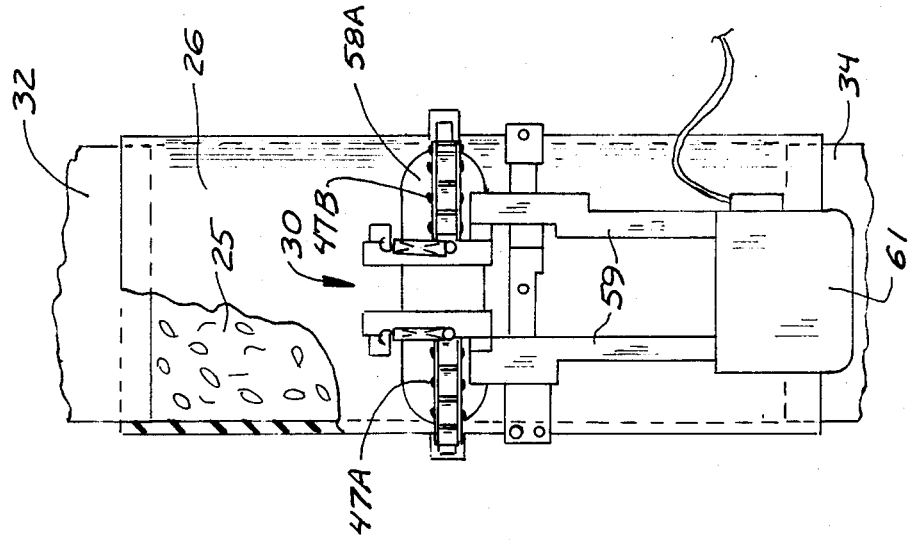

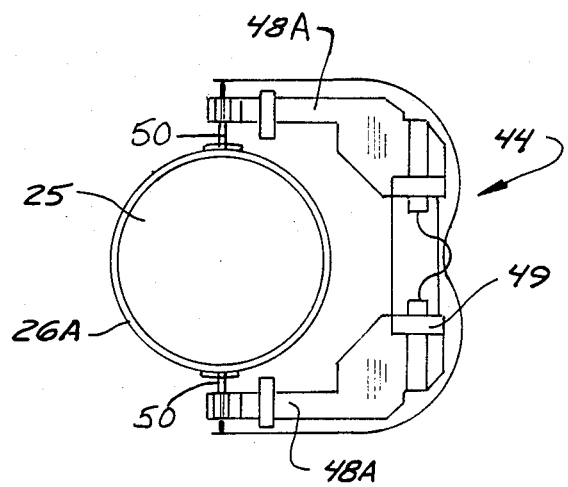
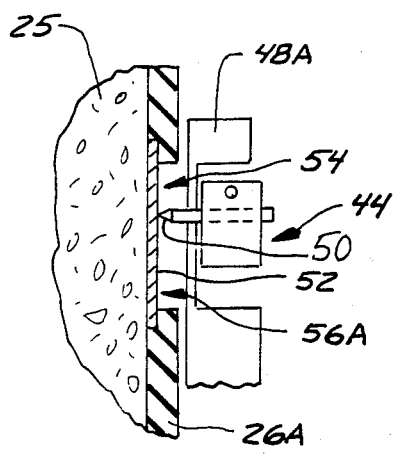
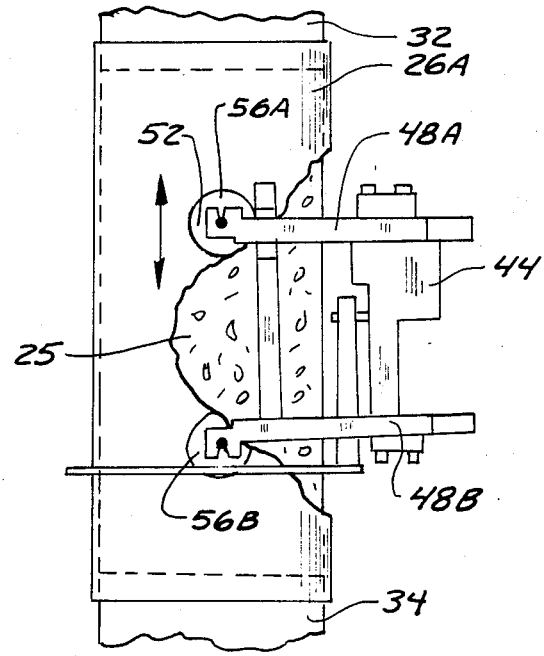

PORTED JACKET FOR USE IN DEFORMATION MEASUREMENT APPARATUS

The U.S. government has rights in this invention pursuant to contract No. DE-AC02-83CH10140 awarded by the U.S. Department of Energy.

BACKGROUND OF THE INVENTION

1. Field of the Invention.

The present invention relates to a device for making an accurate measurement of deformation of a specimen when a jacket to contain the specimen is required.

2. Description of the Prior Art.

Properties of rock and other mineral materials may be determined in controlled laboratory tests. Typically in these tests, a representative specimen of the material is loaded by a testing apparatus. During the test, measurement of the load upon the specimen and measurement of the deformation of the specimen under load are required to characterize the mechanical behavior of the material. To provide accurate measurement of the deformation of the specimen, deformation measurement devices (extensometers) are mounted directly on the specimen under test. Extensometers should directly engage the specimen surface, but usually mineral specimens are jacketed. If the extensometers are mounted on the outer surface of the jacket, the deformation measurement will include a component of deformation contributed by the specimen and also a component of deformation contributed by compression of the jacket.

The mechanical behavior, such as the compression strength of many materials depends on the pressure surrounding the specimen. To simulate such pressure, the specimens are placed inside pressure vessels during test. A space between the specimen and the pressure vessel wall is filled with a fluid which can be pressurized and which may also serve to uniformly heat the specimen. Because of the presence of this pressurizing fluid, the specimen needs to be jacketed to prevent the fluid from contacting the specimen and/or physically or chemically reacting with the specimen.

There are several loading frames for testing the mechanical properties of material. Two such devices are disclosed in Barnaby U.S. Pat. No. 4,562,726, and Heuer, Jr. et al. U.S. Pat. No. 3,199,341, which test for the compressibility of specimens. The disclosures of these two patents show jackets made of a flexible material, but neither shows any sort of contact between a measurement device and the jacket.

Two other prior patents, Lutenegger et al. U.S. Pat. No. 4,122,704 and Handy et al. U.S. Pat. No. 4,047,425, disclose testing devices for measuring lateral expansion induced in a specimen by applying an axial compressive load. The devices shown in these two patents use a cylindrical specimen housing with a slit in the wall of the cylinder. A measuring device is associated with this slit to provide a measurement of lateral expansion. However, neither of these devices includes a flexible jacket around the specimen nor a measurement device making direct contact with such a flexible jacket.

Bishop et al. U.S. Pat. No. 3,505,860 discloses a test apparatus with a fluid pressurized chamber for varying the pressure of the specimen while it is tested. The specimen is contained within a flexible material jacket, but the apparatus does not include an extensometer mounted in direct contact with the material covering the specimen. A similar apparatus is shown in Strom U.S. Pat. No. 3,616,685. Brower et al. U.S. Pat. No. 4,599,891 discloses an apparatus to hold a material specimen.

None of the test systems use a measurement device (extensometer) with a jacketed specimen, where the effects of compressibility of the jacket are eliminated.

SUMMARY OF THE INVENTION

The present invention relates to a specimen jacket adapted to permit accurate measurement of dimensional changes in the specimen within the jacket. The jacket includes a wall of compressible material surrounding the specimen while the specimen is being loaded. At least one port or opening is provided through the wall of compressible material. A thin layer of substantially non-compressible material covers and seals the opening. A measurement device (extensometer) is positioned in contact with the non-compressible material and directly senses the deformation of the specimen.

In one embodiment, two openings in the jacket wall are positioned 180° apart on the wall of the jacket to allow measuring diametrical deformation. The extensometer has contact points which contact the layer of substantially non-compressible material and provide an output signal as the spacing of the contacts changes.

In a second embodiment, the openings in the compressible material jacket are configured to accomodate a circumferential measurement extensometer, which measures lateral deformation, to contact the substantially non-compressible material.

The measurement device contacts the non-compressible material rather than the compressible material, so the measurement by the measurement device (extensometer) contains only the deformation of the specimen, and does not contain a component of deformation contributed by the jacket of compressible material.

BRIEF DESCRIPTION OF THE DRAWINGS

FIG. 3 is a front view of one embodiment of the jacketed specimen having a lateral deformation measuring extensometer thereon;

FIG. 4 is a side view of FIG. 3;

FIG. 7 is a view of a modified jacketed specimen with an axial extensometer mounted thereon;

FIG. 8 is a top view of FIG. 7; and

FIG. 9 is a detailed view of the sensing port of FIG. 7 wherein the axial extensometer contacts the specimen.

DETAILED DESCRIPTION OF THE PREFERRED EMBODIMENTS

Figure 1:
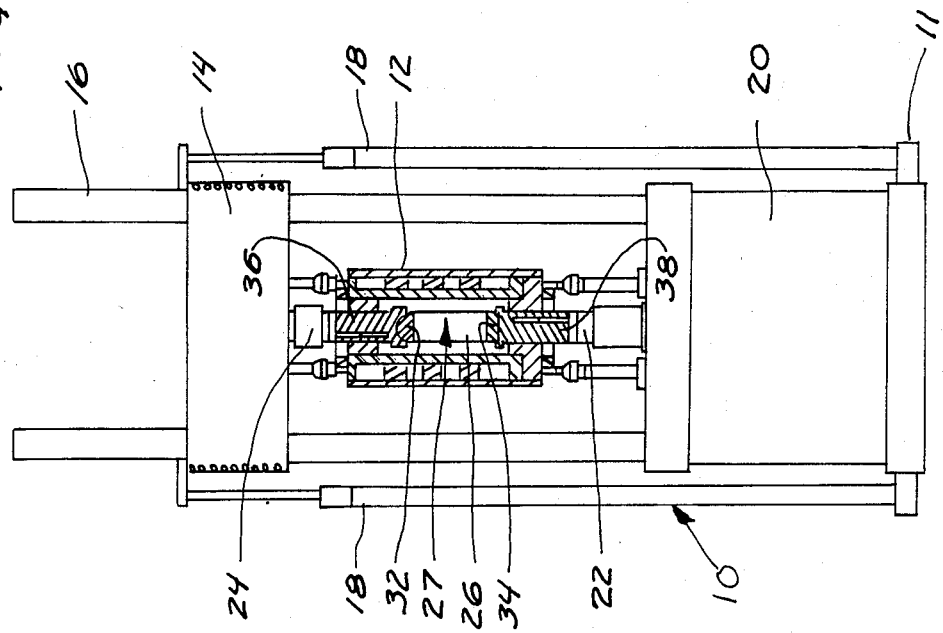
FIG. 1 is a front view of a load frame used to apply a load to a specimen and including a pressure vessel, with parts in section and parts broken away.

In FIG. 1, a typical mineral or rock testing arrangement 10 is shown. The testing arrangement comprises a pressure vessel 12 located within a load frame 11. The load frame 11 includes a movable cross-head 14, movable along upright columns 16 and supported by lift cylinders 18. The lift cylinders 18 are coupled to a base 20 which supports a load applying actuator capable of producing a load upon the specimen being tested within pressure vessel 12. The load is measured through a load cell 24 at the top of the frame and loading ram 22 at the bottom which is connected to the loading actuator. The load cell 24 is supported on the movable cross head 14 for measuring the load applied.

Figure 2:
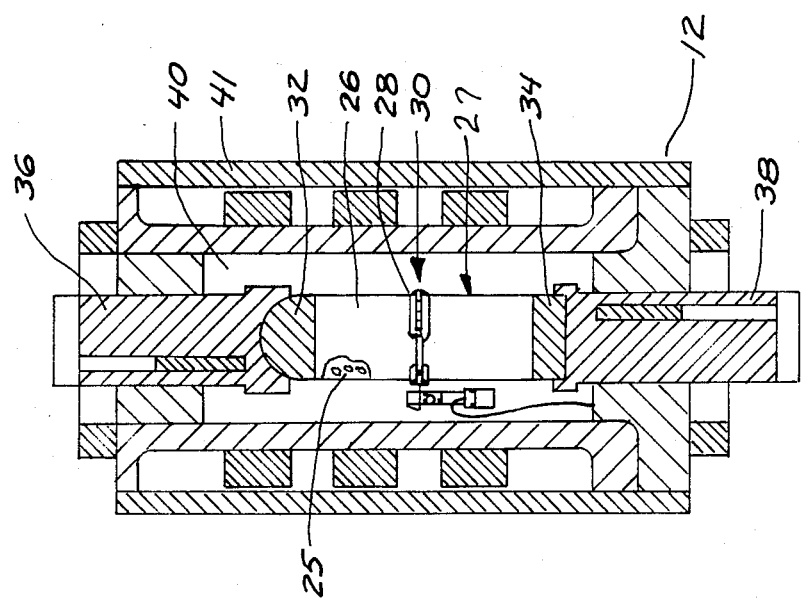
FIG. 2 is an enlarged cross-sectional view of the pressure vessel of FIG. 1.

The pressure vessel 12 is shown in detail in FIG. 2 with a specimen 25 in an outer jacket 26 made according to the present invention in place on the specimen. This forms a jacketed specimen assembly 27. The jacket 26 has a sensing port generally shown at 28 for allowing extensometer or measuring device 30 to be mounted with the sensing section contacting the specimen through the port 28.

The jacket 26 and specimen 25 are loaded in compression through an upper platen 32 and a lower platen 34. The platens support the specimen at the center of the pressure vessel 12. The upper platen 32 and lower platen 34 are coupled to an upper piston 36 and a lower piston 38, respectively, which allow the load frame 20 to apply a load upon the specimen 25. To simulate a surrounding pressure on the jacketed specimen, a fluid 40, which may be heated, is contained within the pressure vessel 12 by the pressure vessel wall 42. The fluid 40 can be pressurized and the pressure will act on the specimen while the load is applied. The load frame, pressure vessel, extensometers and loading pistons are conventional units and are shown only schematically for illustrative purposes.

A diametral extensometer 30, which is illustrated in place on the jacket 26 to sense circumferential changes in the specimen, has a pair of chain sections 47A and 47B (flexible and elongated lines) that are mounted together with fixed sections so the chains engage around the specimen tightly only at two circumferentially extending ports 58A and 58B. The chain sections 47A and 47B have free ends that are held together through the arms 59 of a sensing extensometer 61 of standard design. As the specimen 25 is loaded by the load frame 11, the specimen will change in dimensions, both axially and circumferentially. The measurement device or extensometer 30 is able to measure circumferential deformation at the ports 58A and 58B of the jacketed specimen 25.

Figure 5:
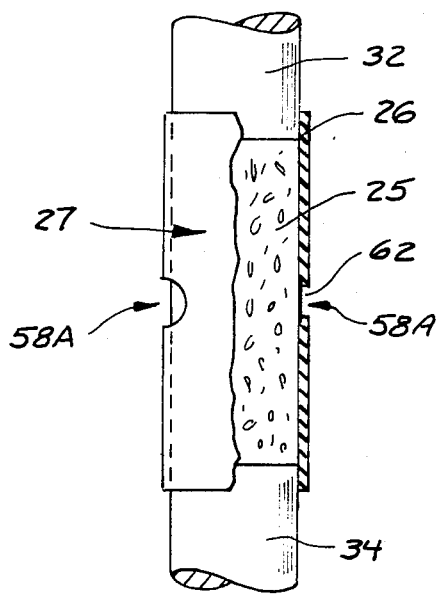
FIG. 5 illustrates a jacket upon the specimen of FIG. 3 with parts in section and parts broken away.
Figure 6:
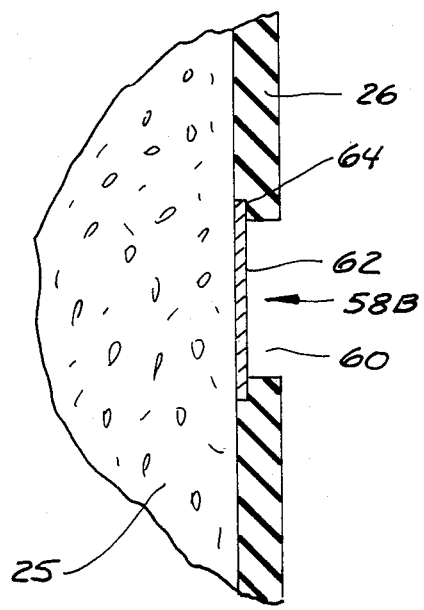
FIG. 6 is a cross-sectional view taken on line 6—6 in FIG. 4.

FIGS. 5 and 6 show the detail of the jacket and specimen. The specimen 25 is surrounded by jacket 26. The jacket 26 is elastomeric and resilient to follow deformation of the specimen when it is loaded by the load frame 11 shown in FIG. 1. The jacket 26 also seals the specimen 25 from liquid in the pressure chamber. The upper platen 32 and lower platen 34 not only provide force transmission from the load frame 11, but the jacket is also sealed with respect to the platens as shown to keep the specimen isolated within the jacket 26. The jacket material is preferably a compressible elastomeric material such as rubber, polyurethane, Viton, etc.

Positioned on the jacket 50 in FIG. 8 is a part-circumferential port 58 which is shown in more detail in FIG. 6. Each port 58A and 58B includes an elongated part-annular opening 60 defined in the jacket 26. A shim 62 of suitable size, slightly larger than the opening 60 is placed to cover the opening 60 at the inner surface of the jacket which contacts the specimen 25, to close and seal the opening 60. The shim is a thin metal, or other material which is substantially less compressible than the elastomeric jacket. The shim can be a hard, flexible plastic, or a suitable metal alloy. The overlapping edges of the shim are sealed or cemented to the jacket.

By closing and sealing the opening 60 with the shim 62, the fluid 40 in the pressure vessel as shown in FIG. 2 is prevented from entering the opening 60 and contacting the specimen 25. The shim 62 is cemented to the inner surface of the jacket 26 at the area 64 surrounding the opening. If the shim is made of copper, steel, or other metal, it is generally about 0.002 to 0.020 inches thick. The shape of the shim 62 varies depending on the test application and the type of extensometer being used for measurement. The shape of the shim 62 and opening 60 must allow the shim 62 to have direct, intimate contact with the extensometer sensing means used, such as the circumferential sensor chain.

FIG. 7, FIG. 8 and FIG. 9 show details of an axial extensometer 44 which measures changes in axial length of the specimen. The extensometer as shown has arms with specimen contact points which align with ports 56A and 56B on the jacket 26A. There are ports 56A and 56B on the opposite sides of the specimen.

The axial extensometer 44 has two sections, one on each side of the specimen, as shown only schematically. The axial extensometer 44 has four arms 48 that are arranged in pairs. Each pair includes an upper arm 48A and a lower arm 48B. The arms 48A and 48B are mounted on a frame 49 that holds the arms. The frame is suitably supported on the test specimen and adjusted so a contact point 50 at the end of each arm 48A and 48B extends into one of the respective ports 56 in the jacket 26A to accomplish the purposes of the present invention.

A detail of one of the ports 56 for the axial extensometer 44 is shown in FIG. 9. The specimen 25 is surrounded by elastomeric jacket 26A. Each port 56 is defined by an opening 54 in the elastomeric jacket wall. A shim 52 is placed at the interior surface of and sealed around the periphery or opening 54 to close the opening. The shim 52 can be made of any desired substantially non-compressible, thin material that will seal the respective opening 54. The specimen contact points 50 of the extensometer 44 are placed in direct contact with the respective shim 52.

The contact points 50 engage the shims 52 tightly and the shim in each port 56 tightly engages the specimen 25. Because the shims 52 are not as compressible as the elastomer (they are substantially less compressible), the points 50 do not compress into the shims 52. Any axial changes in dimension of the specimen are directly sensed by the extensometer.

The jacket 26A tightly engages the specimen 25 and will stretch and move with the specimen, but no compression of the shims 52 interferes with the dimension change sensing.

The jackets 26 or 26A and the respective specimen 25 are placed within the pressure vessel 12 as shown in FIG. 2, once the specimen is assembled with the platens 32 and 34. As the load frame 11 of FIG. 1 applies a load to the specimen 25, the specimen deformation will be accurately measured by the selected measurement device or extensometer. The jacket 26 or 26A will deform with the specimen because of the tight (stretched) fit and the resiliency and conformability of the jacket. The shims 62 or 52, respectively, move to accomodate the deformation of the specimen but does not compress or deform. Since the measurement device or extensometer has contact means in direct contact with the shim 62 or 52, deformation of the specimen 25 will not have a component of deformation contributed by the deformation of the jacket 26 or 26A. The direct transfer of specimen dimension changes through the shims eliminates unknown components of deformation which are not easily quantified. The ported jacket 26 or 26A allows an extensometer to be used virtually as a direct contact measurement device, as there is no component of deformation contributed by the shim at the jacket port where the contact means of the extensometer contacts the ported jacket. By using the ported jacket an accurate material deformation measurement can be made simply, at low cost and without having special extensometers.

While two different forms of ports closed with substantially non-compressible shims are shown, many other types of ported jackets can be utilized for accomodating different types of extensometers. For example, ring type extensometers can be utilized when the entire specimen and jacket are surrounded by a ring that includes contact points at desired annular locations for engaging the specimen through shims and ports in the jacket. Additionally, if rectangular or square cross-section specimens are used for any purpose, the present device can be utilized for providing sensing ports having the shims filling the ports and engaging the specimen wall in the same manner as that shown herein.

For tri-axial tests, both axial and circumferential extensometers are used, so the jacket for such test would have ports for both types of extensometers.

A size of the specimen likewise is not limiting, in that large specimens can be tested in jackets, including tubular specimens that may have ports and sensors on the interior of the tube.

The direction of loading is not a limiting factor in use of the invention, and any type of extensometer or measurement device can be utilized as desired.

Although the present invention has been described with reference to preferred embodiments, workers skilled in the art will recognize that changes may be made in form and detail without departing from the spirit and scope of the invention.

What is claimed is:

1. A device for allowing deformation measurement of a specimen, comprising:
    specimen containment means for surrounding a specimen while the specimen is being loaded, the specimen containment means having a wall of compressible material for allowing deformation of the specimen;
    at least one opening defined in the wall of the compressible material; and
    a thin layer of substantially non-compressible material covering and sealing the opening, wherein measurement means are provided to contact the substantially non-compressible material only for measuring selected dimensional changes of the specimen.

2. The device of claim 1 wherein the opening in the wall of compressible material is configured to allow the measurement means to contact the layer of substantially non-compressible material at a point.

3. The device of claim 2 wherein the opening is elongated circumferentially for the measurement means to contact the substantially non-compressible material along at least a portion of a circumferential line.

4. The device of claim 1 wherein the layer of substantially non-compressible material has an area that is larger than the opening and is sealed around the periphery thereof to the specimen containment means.

5. The device of claim 1 wherein the layer covering and sealing of the opening in the containment means includes securing means for securing the substantially non-compressible material to the compressible material containment means while the specimen and the compressible material are deforming.

6. The device of claim 1 wherein the non-compressible layer comprises a metal shim, and the containment means comprises an elastomeric jacket surrounding the specimen.

7. A method of measuring deformation of a specimen, including:
    providing the specimen to be tested;
    enclosing the specimen within a jacket of elastomeric material having at least one opening and internally contacting the outer surface of the specimen;
    closing the opening by attaching a thin layer of substantially non-compressible material to the jacket portions surrounding the opening, placing the thin layer in contact with the specimen surface; and
    positioning a measurement device on the specimen so that the device contacts only the layer of substantially non-compressible material.

8. The method of claim 7 wherein enclosing the specimen within the jacket of compressible material includes the steps of:
    forming at least two spaced openings in the compressible material, each opening being of a size and shape corresponding to the measurement device structure; and
    configuring the openings to correspond to positions where two portion of the measurement device contact the associated non-compressible material.

9. In a test apparatus for measuring deformation of a specimen, including: a frame for supporting the specimen and providing a load to the specimen, and a measurement device for measuring the deformation of the specimen, the improvement comprising:
    specimen containment means constructed of a compressible material for containing the specimen and having at least one opening; and
    a contact layer constructed of a substantially non-compressible material covering the opening and contacting a specimen in the jacket in the region of the opening and for receiving a portion of the measurement device through the opening.

10. The apparatus of claim 9 wherein the opening is of a size or shape corresponding to the measurement device structure which contacts the specimen containment means.

11. The apparatus of claim 10 wherein the opening is configured in the compressible material to allow the measurement device to contact only the layer of substantially non-compressible material.

12. The apparatus of claim 9 wherein the containment means comprises an enclosing jacket of elastomeric material.

13. A jacket for a mineral specimen to be loaded in a loading device having a measurement device structure for determining deformation of the specimen comprising:
    a jacket wall constructed of a compressible material of size to contain the specimen and having at least one opening; and
    a layer of material constructed of a substantially non-compressible material underlying and closing the opening in the jacket wall and contacting the specimen in the region of the opening, and the layer having a surface exposed through the opening for receiving a portion of a measurement device for determining deformation.

14. The jacket of claim 13 wherein the opening is of a size or shape corresponding to a measurement device structure which contacts the specimen.

15. The jacket of claim 13 wherein there are openings on substantially diametrically opposed sides of said jacket, each of said openings having a contact layer underlying the opening whereby a measurement device can be placed in contact with the specimen through the layer and through each of the openings for measuring diametral deformation.

16. The jacket of claim 13 wherein said layer of material comprises a thin layer of metal underlying the opening and sealed to the jacket wall.

* * * * *